US005705520A

United States Patent [19]

Craig et al.

[11] Patent Number: 5,705,520
[45] Date of Patent: Jan. 6, 1998

[54] MEDICAMENTS

[75] Inventors: Joanne Craig; Derek Leslie Crookes; Stephen John Skittrall, all of Ware, Great Britain

[73] Assignee: Glaxo Group Limited, London, England

[21] Appl. No.: 651,961

[22] Filed: May 21, 1996

Related U.S. Application Data

[63] Continuation of Ser. No. 460,791, Jun. 2, 1995, Pat. No. 5,554,693, which is a continuation of Ser. No. 377,485, Jan. 24, 1995, abandoned, which is a continuation of Ser. No. 66,038, filed as PCT/EP91/02362, Dec. 10, 1991, abandoned.

[30] Foreign Application Priority Data

Dec. 12, 1990 [GB] United Kingdom ............... 9026998

[51] Int. Cl.$^6$ .................... A61K 31/40; C07D 209/14
[52] U.S. Cl. ................................. 514/415; 548/504
[58] Field of Search ........................ 514/415; 548/504

[56] References Cited

FOREIGN PATENT DOCUMENTS

| 0433043 | 3/1991 | European Pat. Off. ....... 548/504 |
| 2162522 | 2/1988 | United Kingdom ........... 548/504 |

OTHER PUBLICATIONS

Dawson, Eur. Naurol., 31, pp. 332–338, 1991.
CA 105 (9): 78831c 3-[2-(Dimethylamino)ethyl]-n-methyl-14-indole-5-methanesulfonamide. Oxford, p. 632, 1986.

*Primary Examiner*—Joseph McKane
*Attorney, Agent, or Firm*—Bacon & Thomas

[57] ABSTRACT

The present invention, relates to 3-[2-(dimethylamino)ethyl]-N-methyl-1H-methanesulphonamide sulphate salt (2:1) and pharmaceutically acceptable solvates thereof, and to pharmaceutical compositions containing same. The compound is useful in the treatment of conditions associated with cephalic pain, in particular migraine. The pharmaceutical compositions are particularly useful as intranasal formulations.

7 Claims, No Drawings

MEDICAMENTS

This application is a continuation of application Ser. No. 08/460,791, filed Jun. 2, 1995, now U.S. Pat. No. 5,554,693, which is a continuation of application Ser. No. 08/377,485, filed Jan. 24, 1995, now abandoned, which is a continuation of application Ser. No. 08/066,038, filed Jun. 14, 1993, now abandoned which is a 371 of PCT/EP91/02362 filed Dec. 10, 1991.

This invention relates to a novel salt of 3-[2-(dimethylamino)ethyl]-N-methyl-1H-indole-5-methanesulphonamide, to pharmaceutical compositions containing it, in particular to compositions adapted for intranasal administration, and to its use in medicine.

3-[2-(dimethylamino)ethyl]-N-methyl-1H-indole-5-methanesulphonamide, which may be represented by the formula (I)

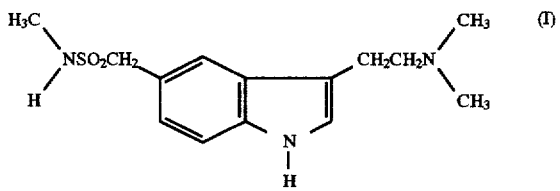

and its physiologically acceptable salts and solvates are disclosed in UK Patent Specification No. 2162522. The compound of formula (I) exhibits selective vasoconstrictor activity and is useful in the treatment of migraine. Physiologically acceptable salts of the compound of formula (I) specifically disclosed in UK Patent Specification No. 2162522 are the succinate, hemisuccinate, fumarate, benzoate, methanesulphonate and hydrochloride salts.

We have now surprisingly found that a particular salt of the compound of formula (I), which falls within the scope of the salts described and claimed in UK Patent Specification No. 2162522 but which is not specifically disclosed therein, is advantageous for the preparation of certain pharmaceutical compositions, in particular for intranasal administration.

The present invention therefore provides 3-[2-(dimethylamino)ethyl]-N-methyl-1H-indole-5-methanesulphonamide sulphate salt (2:1), and physiologically acceptable solvates, including hydrates, thereof.

In an alternative aspect the invention provides a pharmaceutical composition comprising 3-[2-(dimethylamino)ethyl]-N-methyl-1H-indole-5-methanesulphonamide sulphate salt (2:1) or a physiologically acceptable solvate thereof as active ingredient together with a pharmaceutically acceptable carrier therefor.

There is also provided as a further aspect of the invention 3-[2-(dimethylamino)ethyl]-N-methyl-1H-indole-5-methanesulphonamide sulphate salt (2:1) and physiologically acceptable solvates thereof for use in therapy, in particular in human medicine. It will be appreciated that use in therapy embraces but is not necessarily limited to use of 3-[2-(dimethylamino)ethyl]-N-methyl-1H-indole-5-methanesulphonamide sulphate salt (2:1) or a physiologically acceptable solvate thereof as an active therapeutic substance.

In a further aspect there is provided the use of 3-[2-(dimethylamino)ethyl]-N-methyl-1H-indole-5-methanesulphonamide sulphate salt (2:1) or a physiologically acceptable solvate thereof in the preparation of a medicament for use in the treatment of conditions associated with cephalic pain such as cluster headache, chronic paroxysmal hemicrania, headache associated with vascular disorders, headache associated with substances or their withdrawal (for example drug withdrawal), tension headache and in particular migraine.

We have found that the 3-[2-(dimethylamino)ethyl]-N-methyl-1H-indole-5-methanesulphonamide sulphate salt (2:1) or a physiologically acceptable solvate thereof is surprisingly advantageous when administered intranasally.

Oral compositions may be associated with certain disadvantages in the treatment of conditions associated with cephalic pain. For example, such conditions, particularly migraine, are often accompanied by nausea which makes it difficult for a patient to take an oral composition. It is also highly desirable, particularly in the treatment of acute conditions, that pharmaceutical compositions have high bioavailability and a rapid and consistent onset of action. Rapid absorption can be achieved by parenteral administration but this may be unacceptable to some patients, especially if the drug is to be self-administered. Intranasal administration represents a convenient alternative route for administration.

Accordingly, a further aspect of the invention provides a method for the treatment of a mammal, including man, comprising intranasal administration of an effective amount of 3-[2-(dimethylamino)ethyl]-N-methyl-1-indole-5-methanesulphonamide sulphate salt (2:1) or a physiologically acceptable solvate thereof in particular in the treatment of conditions associated with cephalic pain and in alleviating the symptoms associated therewith.

It will be appreciated that reference to treatment is intended to include prophylaxis as well as the alleviation of established symptoms.

Thus, in a preferred aspect the pharmaceutical composition according to the invention is provided in a form adapted for intranasal administration.

Intranasal formulations may generally be provided in liquid or in dry powder forms. Satisfactory intranasal formulations must be sufficiently stable, chemically and physically, to be consistently dispensed in accurate metered doses, even after prolonged storage with potential temperature fluctuations of between 0° and 40° C. Accordingly, the active ingredient must be compatible with the excipients used in the formulation and should not aggregate in a manner which would result in a loss of accurate dose delivery, for example by precipitation from a liquid formulation or by caking of a powder formulation. To maximise retention of an intranasal formulation within the nasal passages of a patient after administration, particularly of a liquid formulation, it is desirable to deliver the unit dosage of active ingredient within a relatively small delivery volume, for example 50–200 µl, preferably 100 µl or less. This may necessitate the use of high concentrations of medicament and highly soluble active ingredients are therefore advantageous. Clearly, an active ingredient must also be presented in a form which is readily absorbed through the nasal mucosa but which is unassociated with any adverse effects such as irritancy.

We have found that for intranasal administration the salt according to the invention may advantageously be administered in the form of a solution.

Solutions will generally be aqueous for example prepared from water alone (for example sterile or pyrogen-free water) or water and a physiologically acceptable co-solvent (for example ethanol, propylene glycol, polyethylene glycols such as PEG 400).

Such solutions may additionally contain other excipients such as preservatives (for example benzalkonium chloride and phenylethylalcohol), buffering agents, isotonicity-adjusting agents (for example sodium chloride), viscosity enhancing agents, absorption enhancers, flavouring agents (for example aromatic flavouring agents such as menthol, eucalyptol, camphor and methyl salicylate in amount of about 0.001 to 0.5% w/w) and sweetening agents (for example saccharin in an amount of about 0.01% w/w to about 10% w/w, preferably in the range of 1 to 5% w/w).

Preferably solutions according to the invention will be sterile and free from preservatives. Sterile formulations may be prepared by methods known in the art, for example by aseptic manufacture or sterilisation of bulk products.

Solutions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution. In the case of a spray this may be achieved for example by means of a metering atomising spray pump.

Intranasal administration may also be achieved by means of an aerosol formulation in which the compound is provided in a pressurised pack with a suitable propellant such as a chlorofluorocarbon (CFC), for example dichlorodifluoromethane, trichlorofluoromethane or dichlorotetrafluoroethane, a hydrofluorocarbon (HFC) for example 1,1,1,2-tetrafluoroethane or 1,1,1,2,3,3,3-heptafluoropropane, carbon dioxide or other suitable gas. The dose of drug may be controlled by provision of a metered valve.

Preferably a pharmaceutical composition containing 3-[2-(dimethylamino)ethyl]-N-methyl-1H-indole-5-methanesulphonamide sulphate salt (2:1) adapted for intranasal administration will be in the form of an aqueous solution.

Aqueous solutions of the salt of the present invention adapted for intranasal administration will preferably have a pH in the range 4 to 8. Most preferably the pH of aqueous solutions of the salt according to the invention for intranasal administration will be 5 to 7, such as 5.4 to 5.6. Adjustment of the pH of aqueous solutions of the hemisulphate salt of the compound of formula (I) to within the desired range is conveniently effected by addition of a base, such as an inorganic base, preferably an alkali metal hydroxide, most preferably sodium hydroxide.

Thus in a particularly preferred aspect the present invention provides an aqueous solution of 3-[2-(dimethylamino) ethyl]-N-methyl-1H-indole-5-methanesulphonamide sulphate salt (2:1) adapted for intranasal administration wherein the pH is in the range of 5 to 7.

It will be appreciated that aqueous solutions of the salt of the present invention may be prepared by dissolving the salt in water. Preferably, however, such solutions are prepared by admixture of 1 molar equivalent of 3-[2-(dimethylamino) ethyl]-N-methyl-1H-indole-5-methanesulphonamide and 0.5 to 0.7 molar equivalent of concentrated sulphuric acid, preferably 0.625 molar equivalent of concentrated sulphuric acid, in water.

Aqueous solutions of the salt of the present invention adapted for intranasal administration will preferably contain the salt in a concentration of 20 mgml$^{-1}$ to 500 mgml$^{-1}$, most preferably 25 mgml$^{-1}$ to 400 mgml$^{-1}$.

It will be appreciated that the precise therapeutic dose of the salt will depend on the age and condition of the patient and the nature of the condition to be treated and will be at the ultimate discretion of the attendant physician.

However, in general effective doses for the treatment of conditions associated with cephalic pain, for example acute treatment of migraine, will lie in the range of 0.5 to 100 mg, preferably 1 to 60 mg, most preferably 2 to 40 mg of the active ingredient per unit dose which could be administered in single or divided doses, for example, 1 to 4 times per day.

The salt of the present invention my conveniently be presented in unit dose form. A convenient unit dose formulation for intranasal administration contains the active ingredient in an amount of from 0.5 mg to 100 mg, preferably in the range of 1 to 60 mg, most preferably 2 to 40 mg, which may be administered to either one or both nostrils. Most preferably, 2.5 mg to 25 mg of the active ingredient is administered in a single dose to one nostril.

A preferred unit dose formulation my be provided as a single dose in a sealed unit, for example a vial of glass or plastics material which may be filled and sealed using conventional manufacturing techniques. Alternatively, a sealed vial of plastics material may be produced by form-fill-seal technology. Preferably the vial and the components of the pharmaceutical formulation filled therein are heat stable. The sealed vial may be sterilised, for example by autoclaving at 121° C. for not less than 15 minutes, to provide a sterile unit dosage vial which can be assembled into a convenient delivery device prior to use. Preferably the unit dose volume is 50 to 200 µl, for example 100 µl.

According to one general process (A), the compound of the present invention or a solvate thereof may be prepared by reaction of 3-[2-(dimethylamino)ethyl]-N-methyl-1H-indole-5-methanesulphonamide or a salt or solvate thereof with sulphuric acid. The process is desirably carried out in aqueous media, optionally in the presence of an organic solvent such as alcohol (for example ethanol or isopropanol). Preferably the compound of the present invention or a hydrate thereof is prepared by admixture of the free base and sulphuric acid in water.

According to another general process (B), the compound of the present invention or a solvate thereof may be prepared by reaction of a salt of 3-[2-(dimethylamino)ethyl]-N-methyl-1H-indole-5-methanesulphonamide or a solvate thereof with an appropriate sulphate salt, for example a metal sulphate (such as sodium or silver sulphate) or a sulphated ion exchange resin, preferably in an aqueous medium.

Such processes (A) and (B) form further aspects of the present invention.

In an alternative aspect of the present invention there is provided a pharmaceutical composition in a form adapted for intranasal administration which comprises an aqueous solution of 3-[2-(dimethylamino)ethyl]-N-methyl-1H-indole-5-methanesulphonamide or a physiologically acceptable salt or solvate thereof, which solution has a pH in the range of pH 5 to pH 7.

A further alternative aspect of the present invention provides a method for the treatment of a mammal, including man, suffering from or susceptible to cephalic pain, in particular migraine, which comprises intranasal administration of a pharmaceutical composition comprising an aqueous solution of 3-[2-(dimethylamino)ethyl]-N-methyl-1H-indole-5-methanesulphonamide or a physiologically acceptable salt or solvate thereof wherein the pH of the solution is in the range of pH 5 to pH 7.

The following non-limiting examples further illustrate the invention.

EXAMPLE 1

3-[2-(Dimethylamino)ethyl]-N-methyl-1H-indole-5-methanesulphonamide sulphate (2:1)

Sulphuric acid solution (2N, 169 ml) was diluted with water (106 ml) and added rapidly dropwise to a stirred solution of 3-[2-(dimethylamino)ethyl]-N-methyl-1H-indole-5-methanesulphonamide (100 g) in ethanol (2.3 l) and water (25 ml) at reflux. The resulting solution was cooled to 45° C.; then seeded, cooled to 4° C. and aged 1 h. The reaction mixture was filtered and the filtrate washed with ethanol (50 ml) then dried at 40° C. in vacuo to give the title compound (114 g) in a solvated form, m.p. 157° C. (decomp.).

Assay shows 6.16% w/w ethanol by G.C.

H.p.l.c. 97.3% corrected, 0.84% w/w water content.

Analysis Found C,47.75: H,6.82; N,11.11; S,13.00

$C_{28}H_{44}N_6O_8S.O.99C_2H_5OH.0.35H_2O$ requires C,48.61; H,6.88; N,11.35; S,12.98%.

The following non-limiting examples illustrate pharmaceutical formulations for intranasal administration according to invention.

EXAMPLES 2 and 3

Sterile Formulation

|  | Example 2 | Example 3 |
|---|---|---|
| Compound of formula (I) | 20 mg | 400 mg |
| Sulphuric Acid (concentrated) BP | 4.23 mg | 84.8 mg |
| Sodium Hydroxide BP | qs to pH 5.4–5.6 | qs to pH 5.4–5.6 |
| Bulk Water for Injections Ph. Eur. | to 1 ml | to 1 ml |

The compound of formula (I) is dissolved in the sulphuric acid previously diluted with water. The solution is made up to approximately 90% of volume. The solution pH is adjusted to 5.5 with sodium hydroxide solution and the solution finally made up to volume. The solution pH is remeasured and adjusted if necessary.

The solution may be packaged for intranasal administration, for example by filling into vials, sealing and sterilising the vials by autoclaving at 121° C. for not less than 15 minutes.

EXAMPLES 4 and 5

Preserved Formulation

|  | Example 4 | Example 5 |
|---|---|---|
| Compound of formula (I) | 25 mg | 400 mg |
| Sulphuric Acid (concentrated) BP | 5.3 mg | 84.8 mg |
| Phenylethyle Alcohol USP | 4 mg | 4 mg |
| Benzalkoniium Chloride USNF | 0.2 mg | 0.2 mg |
| Sodium Hydroxide BP | qs to pH 5.4–5.6 | qs to pH 5.4–5.6 |
| Purified Water B.P. | to 1 ml | to 1 ml |

The compound of formula (I) was dissolved in the sulphuric acid previously diluted with water. Phenylethyl alcohol and benzalkonium chloride were added and the solution made up to approximately 90% of volume. The solution pH was adjusted to 5.5 with sodium hydroxide solution and the solution finally made up to volume. The solution pH was remeasured and adjusted if necessary.

In a similar manner further preserved formulations were prepared containing 5, 10, 50, 100 and 200 mgml$^{-1}$ of the compound of formula (I).

Formulations were administered in unit dose volumes of 100 µl to either one or both nostrils of patients suffering from a moderate or severe migraine attack to deliver a dose of 1, 5, 10, 20 or 40 mg of the compound of formula (I).

EXAMPLES 6 and 7

Sterile Formulation

|  | Example 6 | Example 7 |
|---|---|---|
| Comound of formula (I), sulphate salt (2:1) | 23.2 mg | 465 mg |
| Sodium Hydroxide BP | qs to pH 5.4–5.6 | qs to pH 5.4–5.6 |
| Bulk Water for Injections Ph. Eur. | to 1 ml | to 1 ml |

The compound of formula (I), sulphate (2:1), is dissolved in water and the solution made up to approximately 90% of volume. The solution pH is adjusted to 5.5 with sodium hydroxide solution and the solution finally made up to volume. The solution pH is remeasured and adjusted if necessary.

The solution may be packaged for intranasal administration, for example by filling into vials, sealing and sterilising the vials by autoclaving at 121° C. for not less than 15 minutes.

EXAMPLES 8 and 9

Preserved Formulation

|  | Example 8 | Example 9 |
|---|---|---|
| Compound of formula (I), sulphate salt (2:1) | 23.2 mg | 465 mg |
| Phenylethyl Alcohol USP | 4.0 mg | 4.0 mg |
| Benzalkonium Chloride | 0.2 mg | 0.2 mg |
| Sodium Hydroxide BP | qs to pH 5.4–5.6 | qs to pH 5.4–5.6 |
| Purified Water B.P. | to 1 ml | to 1 ml |

The compound of formula (I), sulphate salt (2:1), is dissolved in water. Phenylethyl alcohol and benzalkonium chloride are added and the solution made up to approximately 90% of volume. The solution pH is adjusted to 5.5 with sodium hydroxide solution and the solution finally made up to volume. The solution pH is remeasured and adjusted if necessary.

EXAMPLES 10 to 13

Sterile Formulation

|  | Example 10 | Example 11 | Example 12 |
|---|---|---|---|
| Compound of formula (I) | 25 mg | 50 mg | 100 mg |
| Sulphuric acid (conc.) BP | 5.3 mg | 10.6 mg | 21.2 mg |
| Bulk Water for Injections Ph. Eur. | to 1 ml | to 1 ml | to 1 ml |

EXAMPLE 13

| Compound of formula (I) | 200 mg |
|---|---|
| Sulphuric acid (conc.) BP | 42.3 mg |
| Bulk Water for Injections Ph. Eur. | to 1 ml |

The compound of formula (I) was dissolved in the sulphuric acid previously diluted with water. The solution was made up to approximately 90% of volume. The solution pH was adjusted to pH 5.4 to 5.6 with sodium hydroxide BP solution and the solution finally made up to volume. The solution pH was remeasured and adjusted if necessary.

The formulations are filled into vials in 100 μl aliquots, the vials are sealed and are sterilised by autoclaving at 121° C. for not less than 15 minutes. The sterile unit dosage vials are assembled into a convenient delivery device prior to use.

The formulations are administered in unit dose volumes of 100 μl to a single nostril of patients suffering from a moderate or severe migraine attack to deliver a dose of 2.5, 5, 10 or 20 mg of the compound of formula (I).

EXAMPLES 14 and 15

Sterile Formulation

|  | Example 14 | Example 15 |
|---|---|---|
| Compound of formula (I) | 200 mg | 200 mg |
| Sulphuric acid (conc.) BP | 42.3 mg | 42.3 mg |
| Sodium Saccharin BP | 10 mg | 20 mg |
| Bulk water for Injections Ph. Eur. | to 1 ml | to 1 ml |

The compound of formula (I) was dissolved in the sulphuric acid previously diluted with water. The solution was made up to approximately 90% of volume and the saccharin dissolved therein. The solution pH was adjusted to pH 5.4 to 5.6 with sodium hydroxide BP solution and the solution finally made up to volume. The solution pH was remeasured and adjusted if necessary.

The formulations are filled into vials in 100 μl aliquots, the vials are sealed and are sterilised by autoclaving at 121° C. for not less than 15 minutes. The sterile unit dosage vials are assembled into a convenient delivery device prior to use.

The formulations are administered in unit dose volumes of 100 μl to a single nostril of patients suffering from a moderate or severe migraine attack to deliver a dose of 20 mg of the compound of formula (I).

EXAMPLES 16 and 17

Sterile Formulations

|  | Example 16 | Example 17 |
|---|---|---|
| Compound of formula (I), Succinate salt (1:1) | 70 mg | 70 mg |
| Sodium saccharin BP | — | 20 mg |
| Bulk Water for Injections Ph. Eur. | to 1 ml | to 1 ml |

The compound of formula I, succinate salt (1:1) is dissolved in water. The solution is made up to approximately 90% of volume and the saccharin dissolved therein. The solution pH is adjusted to pH 5.4 to 5.6 with sodium hydroxide BP solution and the solution finally made up to volume. The solution pH is remeasured and adjusted if necessary.

The solution may be packaged for intranasal administration, for example by filling into vials, sealing and sterilising the vials by autoclaving at 121° C. for not less than 15 minutes.

We claim:

1. 3-[2-(dimethylamino)ethyl]-N-methyl-1H-indole-5-methanesulphonamide hemisulphate salt (2:1) or a physiologically acceptable solvate thereof.

2. A pharmaceutical composition which comprises 3-[2-(dimethylamino)ethyl]-N-methyl-1H-indole-5-methanesulphonamide hemisulphate salt (2:1) or a physiologically acceptable solvate thereof as active ingredient together with a pharmaceutically acceptable carrier.

3. A pharmaceutical composition as claimed in claim 2 adapted for intranasal administration.

4. A method of treating a human suffering from or susceptible to cephalic pain which comprises administration of an effective amount of 3-[2-(dimethylamino)ethyl]-N-methyl-1H-indole-5-methanesulphonamide hemisulphate salt (2:1) or a physiologically acceptable solvate thereof to the human in need thereof.

5. A method according to claim 4 wherein the 3-[2-(dimethylamino)ethyl]-N-methyl-1H-indole-5-methanesulphonamide hemisulphate salt (2:1) or a physiologically acceptable solvate thereof is administered intranasally.

6. A method according to claim 4 wherein the 3-[2-(dimethylamino)ethyl]-N-methyl-1H-indole-5-methanesulphonamide hemisulphate salt (2:1) or a physiologically acceptable solvate thereof is administered in the form of an aqueous solution.

7. A method according to claim 4 wherein the cephalic pain is caused by migraine.

* * * * *

UNITED STATES PATENT AND TRADEMARK OFFICE
CERTIFICATE OF CORRECTION

PATENT NO. : 5,705,520
DATED : January 6, 1998
INVENTOR(S) : CRAIG et al.

It is certified that error appears in the above-identified patent and that said Letters Patent is hereby corrected as shown below:

Column 2, line 22, delete "-1-indole-5-"" and insert therefor -- -1H-indole-5- --.

Column 4, line 4, delete "my" and insert therefor "may".

Signed and Sealed this

Eighth Day of June, 1999

Attest:

Q. TODD DICKINSON

Attesting Officer

Acting Commissioner of Patents and Trademarks